US00PP13358P2

(12) United States Plant Patent
Larsen

(10) Patent No.: US PP13,358 P2
(45) Date of Patent: Dec. 17, 2002

(54) OSTEOSPERMUM PLANT NAMED 'SUNNY NATALIE'

(76) Inventor: Bjarne Nyholm Larsen, Grönnegyden 148, DK-5270 Odense N (DK)

( * ) Notice: Subject to any disclaimer, the term of this patent is extended or adjusted under 35 U.S.C. 154(b) by 0 days.

(21) Appl. No.: 10/096,479

(22) Filed: Mar. 12, 2002

(51) Int. Cl.[7] ..... A01H 5/00
(52) U.S. Cl. ..... Plt./360
(58) Field of Search ..... Plt./360

(56) References Cited

PUBLICATIONS

UPOV ROM GTITM Computer Database, GTI Jouve Retrieval Software Feb. 2002, Citation(s) for PBR001618.*

* cited by examiner

*Primary Examiner*—Bruce R. Campell
*Assistant Examiner*—W C Baker
(74) *Attorney, Agent, or Firm*—C. A. Whealy

(57) ABSTRACT

A distinct cultivar of Osteospermum plant named 'Sunny Natalie', characterized by its upright plant habit; freely branching growth habit; freely flowering habit; and dark purple-colored ray florets.

2 Drawing Sheets

BOTANICAL CLASSIFICATION/CULTIVAR DESIGNATION

*Osteospermum ecklonis* cultivar Sunny Natalie.

BACKGROUND OF THE INVENTION

The present Invention relates to a new and distinct cultivar of Osteospermum plant, botanically known as *Osteospermum ecklonis*, and hereinafter referred to by the name 'Sunny Natalie'.

The new Osteospermum is a product of a planned breeding program conducted by the Inventor in Odense, Denmark. The objective of the breeding program is to create new Osteospermum cultivars with attractive ray and disc floret colors.

The new Osteospermum originated from a self-pollination made by the Inventor in May, 1997 of the *Osteospermum ecklonis* cultivar Sunny Ingrid, disclosed in U.S. Plant Pat. No. 10,996. The new Osteospermum was discovered and selected by the Inventor as a single flowering plant within the progeny of the stated cross grown in a controlled environment in Odense, Denmark in November, 1997.

Asexual reproduction of the new Osteospermum by terminal vegetative cuttings was first conducted in Odense, Denmark in May, 1998. Asexual reproduction by cuttings has shown that the unique features of this new Osteospermum are stable and reproduced true to type in successive generations.

SUMMARY OF THE INVENTION

The cultivar Sunny Natalie has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Sunny Natalie'. These characteristics in combination distinguish 'Sunny Natalie' as a new and distinct Osteospermum:

1. Upright plant habit.
2. Freely branching growth habit.

3. Freely flowering habit.
4. Dark purple-colored ray florets.

Plants of the new Osteospermum are most similar to plants of the parent, the cultivar Sunny Ingrid. Plants of the new Osteospermum and the cultivar Sunny Ingrid differ primarily in ray floret color.

BRIEF DESCRIPTION OF THE PHOTOGRAPHS

The accompanying colored photographs illustrate the overall appearance of the new Osteospermum showing the colors as true as it is reasonably possible to obtain in colored reproductions of this type. Colors in the photographs may differ from the color values cited in the detailed botanical description which accurately describe the colors of the new Osteospermum.

The photograph on the first sheet comprises a side perspective view of a typical flowering plant of 'Sunny Natalie'.

The photograph on the second sheet is a close-up view of typical inflorescences and leaves of 'Sunny Natalie'. The colors in the photograph on the second sheet are closer to the actual colors than the colors in the photograph on the first sheet.

DETAILED BOTANICAL DESCRIPTION

The aforementioned photographs and following observations and measurements describe plants grown in Odense, Denmark, in a glass-covered greenhouse ruing the late spring and early summer with day and night temperatures averaging 20° C. and light levels about 5,000 lux. After planting rooted cuttings, plants were grown for about 13 to 14 weeks in 12-cm containers with one plant per container. Color references are made to The Royal Horticultural Society Colour Chart, 1995 edition, except where general terms of ordinary dictionary significance are used.

Botanical classification: *Osteospermum ecklonis* cultivar Sunny Natalie.

Parentage: Self-pollination of *Osteospermum ecklonis* cultivar Sunny Ingrid, disclosed in U.S. Plant Pat. No. 10,996.

Propagation:

*Type.*—Terminal vegetative cuttings.

*Time to initiate rooting.*—About 10 days at 20° C.

*Time to develop roots.*About 21 days at 20° C.

*Root description.*—Fine, fibrous and well-branched.

Plant description:

*Appearance.*—Perennial herbaceous container and garden plant. Upright and outwardly spreading plant habit. Freely branching, at least ten lateral branches develop after pinching; dense and full plants. Moderately vigorous growth habit.

*Plant height.*—About 40 cm.

*Plant width or area of spread.*—About 60 cm.

*Lateral branches.*—Length: About 35 cm. Diameter: About 3 mm. Internode length: About 1.5 cm. Aspect: Upright to outward. Strength: Strong, but flexible. Texture: Pubescent. Color: Close to 143C.

*Foliage description.*—Arrangement: Alternate; simple. Length: About 7 cm. Width: About 2.5 cm. Shape: Oblanceolate. Apex: Acute to cuspidate. Base: Attenuate. Margin: Entire with occasional tiny teeth. Venation pattern: Pinnate. Texture, upper and lower surfaces: Pubescent. Fragrance: Strong, typical of species. Color: Young and fully expanded foliage, upper surface: Close to 136A; venation, close to 136A. Young and fully expanded foliage, lower surface: Close to 137C; venation, close to 137C. Petiole: Length: About 1 cm. Diameter: About 5 mm. Texture, upper and lower surfaces: Glabrous. Color, upper surface: Close to 136A. Color, lower surface: Close to 137C.

Inflorescence description:

*Appearance.*—Terminal and axillary inflorescences held above and beyond the foliage on moderately strong peduncles. Composite inflorescence form, radially symmetrical; ray and disc florets arranged acropetally on a capitulum. Inflorescences persistent. Inflorescences face upright or outward.

*Flowering response.*—Plants flower continuous and freely from the spring through the fall.

*Postproduction longevity.*—Inflorescences maintain good color and substance for about one week on the plant.

*Quantity of inflorescences.*—Freely flowering; at one time, about ten open inflorescences and inflorescence buds per lateral stem.

*Fragrance.*—Slight, typical of species.

*Inflorescence bud* (*at stage of showing color*).—Length: About 1.5 cm. Diameter: About 1 cm. Shape: Ovoid. Color, ray florets, lower or outer surface: Close to 187A.

*Inflorescence size.*—Diameter: About 6 cm. Depth (height): About 2 cm. Disc diameter: About 1 cm.

*Ray florets.*—Length: About 3 cm. Width: About 7.5 mm. Shape: Oblanceolate. Apex: Rounded or slightly emarginate. Base: Attenuate. Margin: Entire. Texture, upper and lower surfaces: Smooth, satiny. Orientation: Initially upright then about 70° from vertical. Number of ray florets per inflorescence: About 19 in a single whorl. Color: When opening and fully opened, upper surface: 187A. When opening and fully opened, lower surface: 187A to 187B.

*Disc florets.*—Shape: Tubular, elongated. Apex: Five-pointed. Length: About 7 mm. Width: At apex: About 2.5 mm. At base: About 1 mm. Number of disc florets per inflorescence: More than 50. Color: Immature: Close to 94A. Mature: Close to 89A.

*Phyllaries.*—Length: About 2 cm. Diameter: About 1.5 mm. Shape: Narrowly lanceolate. Apex: Acute. Base: Fused. Margin: Entire. Texture, upper and lower surfaces: Coarse, pubescent. Number per inflorescence: About 20 in a single whorl. Color, upper and lower surfaces: 144A.

*Peduncles.*—Length, terminal peduncle: About 14 cm. Diameter: About 2 mm. Angle: Erect. Strength: Strong. Texture: Rough, slightly pubescent. Color: 144A.

*Reproductive organs.*—Androecium: Present on disc florets only. Stamen number: Five per floret; fused around style. Anther shape: Oblong. Anther length: About 1 mm. Anther color: 95B. Pollen amount: Moderate. Pollen color: Close to 23A. Gynoecium: Present on both ray and disc florets. Pistil number: One per floret. Pistil length: About 7.5 mm. Stigma shape: Two-parted. Stigma color: Close to 83A. Style length: About 5 mm. Style color: Close to 84C. Ovary color: Close to 145A.

*Seed/fruit.*—Seed and/or fruit production has not been observed.

Disease/pest resistance: Resistance to pathogens and pests common to Osteospermums has not been observed on plants grown under commercial greenhouse or outdoor conditions.

Temperature tolerance: Plants of the new Osteospermum have been observed to tolerate temperatures from 1 to more than 35° C.

It is claimed:

1. A new and distinct cultivar of Osteospermum plant named 'Sunny Natalie', as illustrated and described.

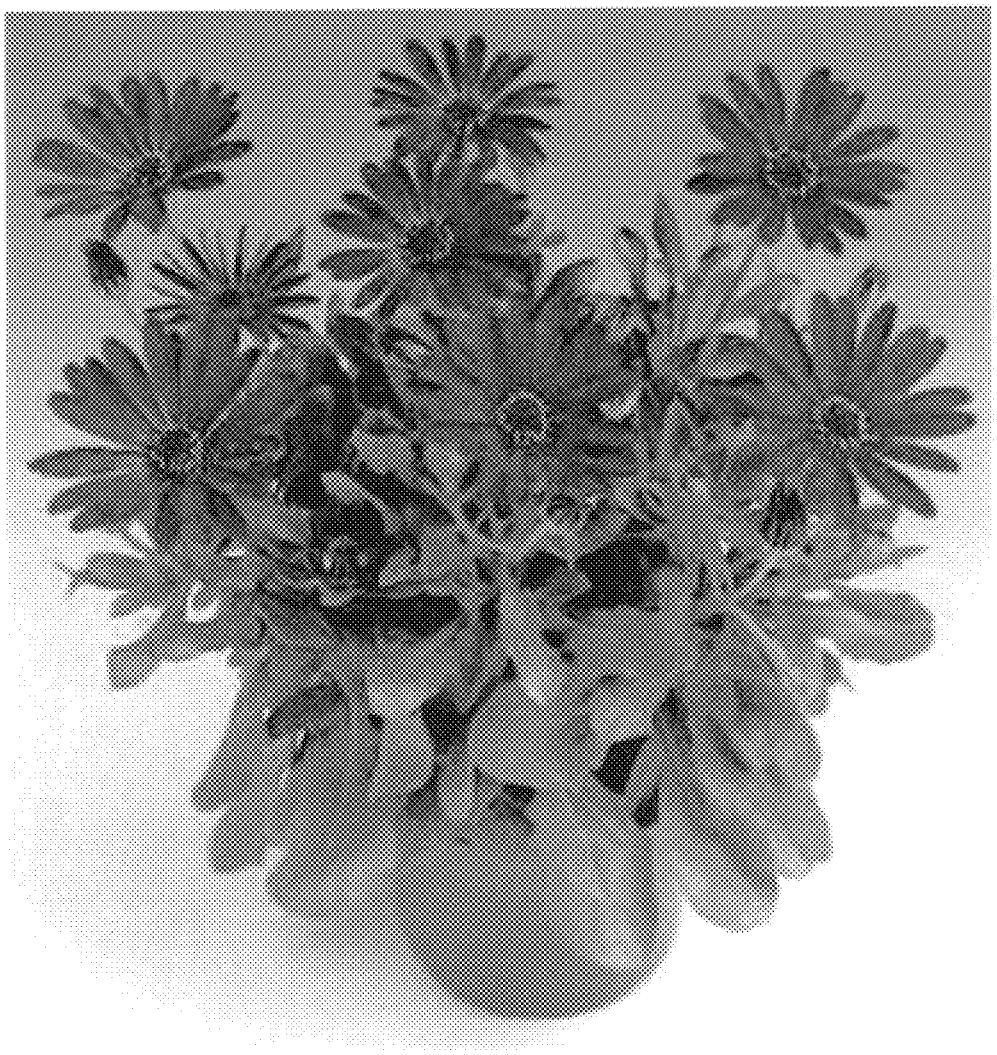

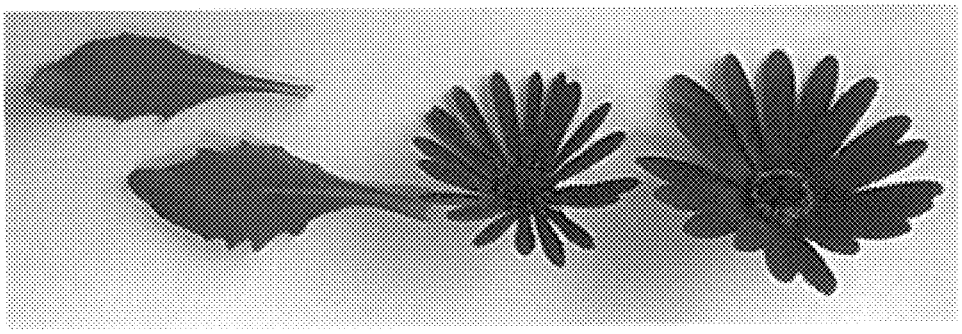

* * * * *